United States Patent
Clarke et al.

(10) Patent No.: US 6,387,512 B1
(45) Date of Patent: May 14, 2002

(54) GREY COLORING PHOTOCHROMIC FUSED PYRANS

(75) Inventors: David Allan Clarke, Brighouse; Bernard Mark Heron, Yorkshire; Christopher David Gabbutt; John David Hepworth, both of Lancashire; Steven Michael Partington; Stephen Nigel Corns, both of Huddersfield, all of (GB)

(73) Assignee: James Robinson Limited, Huddersfield (GB)

( * ) Notice: Subject to any disclaimer, the term of this patent is extended or adjusted under 35 U.S.C. 154(b) by 0 days.

(21) Appl. No.: 09/787,362

(22) PCT Filed: Aug. 24, 1999

(86) PCT No.: PCT/GB99/02788

§ 371 Date: Mar. 16, 2001

§ 102(e) Date: Mar. 16, 2001

(87) PCT Pub. No.: WO00/18755

PCT Pub. Date: Apr. 6, 2000

(30) Foreign Application Priority Data

Sep. 29, 1998 (GB) .............................................. 9821121

(51) Int. Cl.$^7$ ..................... C07D 311/82; C07D 401/00; B73B 27/36; C10C 1/18; C09K 3/00

(52) U.S. Cl. ..................... 428/426; 428/500; 428/913; 44/329; 44/332; 106/27; 106/31.47; 106/31.49; 540/477; 540/480; 540/481; 540/576; 540/581; 544/129; 544/141; 546/187; 546/195; 546/196; 546/198; 546/202; 546/246; 546/247; 546/248

(58) Field of Search ................................. 549/388, 389, 549/391, 392, 393, 394, 41, 42; 546/187, 195, 196, 198, 202, 246, 247, 248; 548/416, 424, 426, 517, 525, 527; 544/129, 141; 540/477, 480, 481, 576, 581; 44/329, 332; 106/31.47, 31.49, 27; 428/913, 426, 500

(56) References Cited

U.S. PATENT DOCUMENTS 5,658,500 A  8/1997  Kumar et al. ............... 549/389

FOREIGN PATENT DOCUMENTS

| EP | 0562915 | 9/1993 | ................. 549/389 |
| WO | 9420869 | 9/1994 | ................. 549/389 |
| WO | 9604576 | 2/1996 | ................. 549/389 |
| WO | 9804937 | 2/1998 | ................. 549/389 |
| WO | 9842693 | 10/1998 | ................. 549/389 |
| WO | 9842695 | 10/1998 | ................. 549/389 |
| WO | 9931081 | 6/1999 | ................. 549/389 |

*Primary Examiner*—Alan L. Rotman
*Assistant Examiner*—Raymond Covington
(74) *Attorney, Agent, or Firm*—Stevens, Davis, Miller & Mosher, L.L.P.

(57) ABSTRACT

A photochromic grey coloring 2H-naphtho[1,2-b]pyran of formula (1) wherein $R^1$ is selected from mono-, di- or poly-substituted aryl groups, mono-, di- or poly-substituted naphthyl groups and mono-, di- or poly-substituted heteroaryl groups, wherein at least one substituent is a nitrogen containing group, including amino, $C_1$–$C_{20}$ and $C_6$–$C_{20}$ alkylamino, $C_1$–$C_{20}$ and $C_6$–$C_{20}$ dialkylamino, $C_2$–$C_{20}$ dialkenylamino, $C_2$–$C_{20}$ or $C_4$–$C_{20}$ di(polyalkenyl)amino, arylamino, diarylamino, $C_1$–$C_{20}$ alkylarylamino, tetra ($C_1$–$C_{10}$ linear or branched alkyl) guanidino and cyclic-amino groups and at least one of $R^7$ and $R^9$, which may be the same or different, is selected from $C_1$–$C_{20}$ N alkylamino $C_1$–$C_{20}$ N-alkylamido, $C_1$–$C_{20}$ N,N-dialkylamido, amido, nitro, amino, $C_1$–$C_{20}$ alkylamino, $C_1$–$C_{20}$ dialkylamino, $C_2$–$C_{20}$ dialkenylamino, $C_4$–$C_{20}$ di(polyalkenyl)amino, arylamino, diarylamino, $C_1$–$C_{20}$ alkylarylamino, or cyclicamino groups. The compounds may be combined with a polymeric host material such as plastic or glass to make a sunglass lens, an ophthalmic lens or a window. The compounds may also be included in an ink or a fuel.

15 Claims, No Drawings

GREY COLORING PHOTOCHROMIC FUSED PYRANS

PRIORITY CLAIM

This application is a §371 application, claiming priority from PCT International Application No. WO 00/18755, filed Aug. 24, 1999 and Great Britain Application No. 9821121.2, filed Sep. 29, 1998.

The present invention relates to new grey colouring photochromic fused pyrans and to their use.

Photochromism is a well-known physical phenomenon that is observed with certain classes of chemical compounds. A detailed discussion of this phenomenon can be found in "Photochromism: Molecules and systems", Studies in Organic Chemistry 40, Eds. H. Durr and H. Bouas-Laurent, Elsevier, 1990.

The 2H-naphtho[1,2-b]pyran system is known to be capable of exerting a photochromic effect as described, for example, in U.S. Pat. Nos. 3,567,605 and 4,826,977. U.S. Pat. No. 3,567,605 provides an example of a naphtho[1,2-b]pyran which remains coloured at ambient temperatures for several hours, and U.S. Pat. No. 4,826,977 describes a series of yellow/orange colouring 2H-naphtho[1,2-b]pyrans containing a spiro-adamantane group at the 2-position amongst other 2H-[1] benzopyran and isomeric naphthopyran systems. The basic structural unit of the 2H-naphtho[1,2-b] pyran system, in this instance substituted at C-2 with a spiro-adamantane group, is illustrated below.

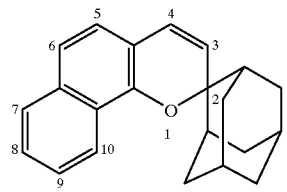

A range of purple/blue colouring 2(4-aminophenyl)-2-alkyl-2H-naphtho[1,2-b]pyrans have also been described in U.S. Pat. No. 4,818,096.

A series of photochromic 2H-naphtho[1,2-b]pyrans, amongst other 2H[1]benzopyrans and isomeric naphthopyrans, bearing a cyclopropyl group as one of the substituents at the 2-position is described in patent publication WO92/01959. It is also commented that the compound 2-cyclopropyl-2-p-methoxyphenyl-5-methyl-2H-naphtho[1,2-b]pyran and several other analogues are of particular current interest, but no reasons are presented either to substantiate such interest or as to any significance of the 5-methyl group.

It is stated in U.S. Pat. No. 5,066,818 (1991) that "The compound, 2,2-diphenyl-2H-naphtho[1,2-b]pyran, also colours on exposure to near ultraviolet light at room temperature but does not bleach in a reasonable period of time. Substitution of the phenyl substituents in the meta and para positions have little effect on the rate of bleaching of these compounds."

The very high optical density of 2,2-diaryl-2H-naphtho [1,2-b]pyrans achieved under irradiation and their slow attendant fade (bleaching) on removal of the source of irradiation relative to the photochromic properties display:ed by the isomeric 3,3-diaryl-3H-naphtho[2,1-b]pyrans has been noted by B. van Gemert et al. (*Mol. Cryst. Liq. Cryst.* 1994, 246, 67). The relatively slow attendant fade of the 2,2-diaryl-2H-naphtho[1,2-b]pyrans was rationalised by the absence of steric crowding in the ring opened (coloured) quinoidal/zwitterionic forms. Such steric crowding is thought to be present for the ring opened form of the 3,3-diaryl- 3H-naphtho[2,1-b]pyrans and accounts for their relatively rapid fade.

Pilkington Plc have also commented on the fading of photochromic materials in Research Disclosure {May (1994), No. 36144, p 267}. This disclosure reports that markedly improved rates of fade can be obtained for 2,2-diaryl-2H-naphtho[1,2-b]pyrans bearing substituents at both the 5- and 6- positions compared with 2,2-diaryl-2H-naphtho[1,2-b]pyrans that are unsubstituted at these sites. These substituents are reported to exert steric pressures upon the ring opened (coloured) forms and enhance the ring closure to the uncoloured naphthopyran system. However, these relatively fast fading materials described by Pilkington Plc with substituents at both the 5- and 6- positions are difficult to manufacture, requiring a long multi-stage process which renders them unattractive commercially. Thus the use of two substituents at the 5- and 6- positions to achieve rapid fade in these 2,2-diaryl compounds has the disadvantage of manufacture complexities.

Two more recent U.S. Pat. Nos. 5,458,814 and 5,514,817 describe the synthesis of a range of fast fading intense yellow to red/purple colouring 2,2-diaryl-2H-naphtho[1,2-b]pyrans and phenanthropyrans which either possess a 5-substituent or are 5,6-disubstituted.

Other 5-substituted rapid fading intense colouring photochromic naphtho[1,2-b]pyrans are included in U.S. Pat. No. 5,658,500 (1997). These naphthopyrans, which may also include an aminoaryl group at position 2, can be used in conjunction with other complementary photochromic materials so that together a near neutral grey or brown shade is developed when a lens containing such a mixture is subjected to UV light. Some naphtho[1,2-b]pyrans which may also contain aminoaryl groups at position 2 and are further substituted at position 2,7 and 9 with alkoxy groups have been described in application PCT WO 98/04937. These molecules are attributed with the beneficial properties of higher lambda max values for both of their absorption bands and also have a generally higher induced optical density compared with molecules which do not possess the di-alkoxy substitution pattern.

International patent application WO 95/05382, describes some neutral colouring, typically brown, photochromic heterocyclochromenes in which the hetero ring is fused to either the f- or g-face of the benzopyran unit. No examples or claims pertaining to the h- fused isomers were made. A range of f-fused heterocyclic pyrans has been described in U.S. Pat. No. 5,527,911 (1996). The examples reported in this work all possess unsubstituted phenyl groups at C-2 in the pyran ring and provide orange or red colouring compounds. A subsequent U.S. Pat. No. 5,552,091 (1996) claims f-, g- and h- fused benzofuro-, benzothieno- and indolo-benzopyrans. In all examples, regardless of the mode of ring fusion, C-2 of the pyran ring is substituted with at least one of the following tricyclic moieties: fluorenyl, dibenzofuryl, dibenzothienyl or carbazolyl. No examples of C-2 (monocyclic) diaryl substituents are claimed in this work. An additional PCT, WO 94/20869, also describes f-, g- and h- fusions of benzothiophene and benzofuran to 2,2-diaryl benzopyrans. None of the reported examples pertain to heterocyclic fused 2,2-diaryl benzopyrans in which the pendant aryl groups possess one or more cyclic amino substituents located in the para position.

In International patent application no. PCT/GB98/00904, there are described the synthesis and applications of some neutral colouring (brown or brown/red) photochromic 2,2-diaryl-2H-naphtho[1,2-b]pyrans. The brown or brown/red colouring is obtained by substituting the 2,2-diaryl-2H-naphtho[1,2-b]pyrans in the 7- and/or 9- position with an amino function. The general formula in PCT/GB98/00904 also covers brown or brown/red compounds in which one or both of the 2,2-diaryl groups may be unsubstituted, mono-, di- or poly-substituted and among the possible substitutents are amino, amino $C_1$–$C_5$ alkyl, alkyl $C_1$–$C_5$ amino, dialkyl $C_1$–$C_5$ amino and certain cyclic amino groups. However, there are no specific Examples of such compounds, but only of 2,2-diaryl alkoxy substituted compounds.

We have now found that, surprisingly, photochromic 2,2-diaryl-2H-naphtho[1,2-b]pyrans wherein at least one of the aryl groups is substituted with an amino function, preferably in the para position to the point of attachment to the pyran ring, in addition to amino function substitution at the 7- and/or 9- position, exhibit neutral non-brown, non-brown/red colouring which is quite different from the neutral brown or brown/red described in PCT/GB98/00904. The presence of a 5 substituent in these pyrans may also provide for rapid fading of the colour generated upon irradiation.

The neutral non-brown, non-brown/red colours observed in the photochromic compounds of the invention are typically various shades and hues of grey, blue grey, purple grey, green grey and, on occasion, approach black. They typically result from multiple absorption bands at about 460–520 nm and about 550–650 nm upon irradiation with sunlight or a suitable artificial light source. The bands are often broad and may overlap.

The provision of grey colouring photochromic compounds is highly advantageous. Previously, to achieve, for example, grey colouring, it was necessary to mix two or more compounds. A disadvantage of mixing two or more compounds is that it is very difficult to obtain a uniform grey at all times in the bleach/fade cycle.

The neutral non-brown, non-brown/red, which we shall refer to hereinafter as grey, compounds of the present invention provide photochromic materials with good rates of fade over a broad range of temperatures and intense neutral colour generation accompanied by negligible background colour. These features render these compounds particularly useful as photochromic materials for incorporation into polymeric host materials since the amount of photochromic material required to impart a useful photochromic effect into the host material may be greatly reduced, thereby offering a considerable saving of synthetic effort and cost over conventional materials which do not possess the claimed substitutents.

Examples of applications of the polymeric host materials of the present invention include the manufacture of lenses for sunglasses and ophthalmic lenses, protective visors, screens, films, 'plastic' sheeting, containers (e.g. bottles and other packaging vessels), mirrors, windows and screens for vehicles such as cars (including sunroofs), motorcycles, aircraft and ships, architectural uses e.g. glazing, and artistic 'stained glass' windows and for use in novelty items. Additionally the materials may be used in vehicle body panels including fairings and spoilers, and related external surfaces and other embodiments where it may be deemed attractive to have said objects change colour in the presence of sunlight. A further use is their incorporation into inks and other such formulations for 'printing' onto paper and fabrics and other suitable surfaces. This latter application may be particularly useful for the preparation of security markers (labels) on a broad range of objects e.g. cheques, bonds, bankers drafts, credit cards, charge cards and identity documents and cards. Such inks and other like formulations may be used for printing documents and greetings cards. The security/identity uses of these photochromic compounds may also extend to include the marking of fuels e.g. petrol and diesel and other oils. Furthermore, the materials may be used in optical data recording systems e.g. compact discs, and read/write optical data storage discs, as waveguides and laser dyes.

Typical host materials are optically clear or opaque polymer materials, such as polymers of polyol (alyl carbonate)-monomers, polyacrylates such as polymethylmethacrylates, poly(triethyleneglycol dimethylacrylate), polyperfluoro-acrylates and cellulose acetate, cellulose triacetate, cellulose acetate propionate, cellulose acetate butyrate, poly(vinyl acetate), poly(vinyl alcohol), polyurethanes, polycarbonate, polyethylene terephthalate, polystyrene, polyfluorostyrene, poly(diethyleneglycol bis(alkyl carbonate)) and various copolymer mixes.

According to the present invention, there is provided a photochromic compound of the formula I

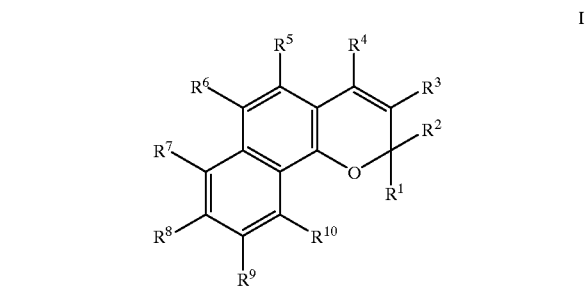

I

In formula I above $R^1$ is selected from mono-, di- or poly-substituted aryl groups, mono-, di- or poly- substituted naphthyl groups and mono-, di- or poly- substituted heteroaryl groups (for example but not exclusively thienyl, benzothienyl, furyl, benzofuryl, pyrryl, indolyl, pyridyl, quinolyl, isoquinolyl, pyrimidyl, oxazolyl, isoxazolyl, thiazolyl, isothiazolyl, pyrazolyl, imidazolyl, benzimidazolyl, triazolyl, benzotriazolyl, tetrazolyl). The substituents for the aryl, naphthyl and heteroaryl groups representing $R^1$ are selected from the following nitrogen containing functionalities and are situated preferentially in a conjugating position, typically para to the point of attachment to the pyran ring: amino $C_1$–$C_{20}$ alkylamino, $C_1$–$C_{20}$ dialkylamino, $C_2$–$C_{20}$ dialkenylamino, $C_2$–$C_{20}$ di(polyalkenyl)amino, arylamino, diarylamino, $C_1$–$C_{20}$ alkylarylamino, tetra($C_1$–$C_{10}$ linear or branched alkyl) guanidino and cyclic-amino groups (for example but not exclusively aziridino, pyrrolidino, piperidino, linear or branched $C_1$–$C_{20}$ alkylsubstituted piperidino, morpholino, thiomorpholino, indolino, piperazino, linear or branched $C_1$–$C_{20}$ N-alkylpiperazino, linear or branched $C_1$–$C_{20}$ N-hydroxyalkylpiperazino, N-phenylpiperazino, N-arylpiperazino, homopiperidino). In addition to the above nitrogen containing function, $R^1$ may also possess one or more additional substituents which are selected from hydrogen, linear or branched $C_1$–$C_{20}$ alkyl, $C_3$–$C_{20}$ cycloalkyl, $C_4$–$C_{20}$ bicycloalkyl (for example but not exclusively norbornyl), $C_5$–$C_{20}$ polycycloalkyl (for example but not exclusively adamantyl), linear or branched $C_1$–$C_{20}$ haloalkyl, linear or branched $C_1$–$C_{20}$ perhaloalkyl, linear or branched $C_2$–$C_{20}$ alkenyl (E or Z isomers), linear or branched $C_2$–$C_{20}$ polyalkenyl (any combinations of E or Z isomers), linear or branched $C_2$–$C_{20}$ alkynyl, linear or branched $C_4$–$C_{20}$ polyalkynyl, linear or branched $C_1$–$C_{20}$ hydroxyalkyl, linear or branched $C_1$–$C_{20}$ polyhydroxyalkyl, linear or branched $C_1$–$C_{20}$ alkoxy, linear or branched $C_1$–$C_{20}$ alkylthio, linear or branched $C_1$–$C_{20}$($C_1$–$C_5$ alkoxy) alkyl, linear or branched $C_1$–$C_{20}$($C_1$–$C_5$ alkylthio)alkyl, phenyl, aryl, heteroaryl, halogen, hydroxyl, formyl, acetyl, nitrile, carboxyl, $C_1$–$C_5$ alkoxycarbonyl, $C_1$–$C_5$ N-alkylamido, $C_1$–$C_5$ N,N-dialkylamido, amido, nitro, amino, $C_1$–$C_{20}$ alkylamino, $C_1$–$C_{20}$ dialkylamino, $C_2$–$C_{20}$ dialkenylamino, $C_4$–$C_{20}$ di(polyalkenyl)amino, arylamino, diarylamino, $C_1$–$C_{20}$ alkylarylamino, and cyclic-amino groups (for example but not exclusively aziridino, pyrrolidino, piperidino, linear or branched $C_1$–$C_{20}$ alkylsubstituted piperidino, morpholino, thiomorpholino, indolino, piperazino, linear or branched $C_1$–$C_{20}$ N-alkylpiperazino, linear or branched $C_1$–$C_{20}$ N-hydroxyalkylpiperazino, N-phenylpiperazino, N-arylpiperazino, homopiperidino), arylsulfanyl, aryloxy, arylsulfinyl, arylsulfonyl, linear or branched $C_1$–$C_{20}$ alkylsulfonyl, di-($C_1$–$C_{20}$ alkoxyalkyl) phosphonyl. Phenyl, aryl, naphthyl, and heteroaryl ring substituents may be located at the ortho-, meta- or para- positions. $R^1$ and or $R^2$ may also be selected from the fused saturated heterocycles II, III and IV in which n and m are integers between 2 and 5 and may be the same or different.

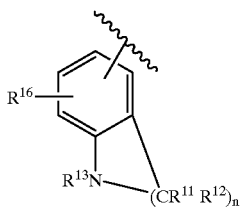

II

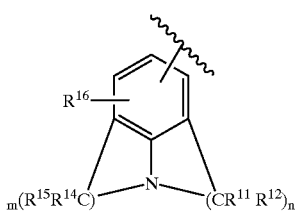

III

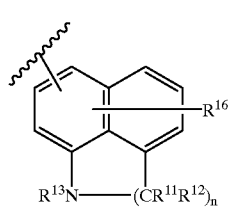

IV $R^{13}$ may be selected from linear or branched $C_1$–$C_{20}$ alkyl, $C_3$–$C_{20}$ cycloalkyl, $C_4$–$C_{20}$ bicycloalkyl, $C_5$–$C_{20}$ polycycloalkyl, linear or branched $C_1$–$C_{20}$ hydroxyalkyl, linear or branched $C_1$–$C_{20}$ haloalkyl, linear or branched $C_1$–$C_{20}$ perhaloalkyl, phenyl, $C_1$–$C_{20}$ linear or branched alkylsulfonyl, aryl, tosyl, arylsulfonyl, acyl, linear or branched $C_1$–$C_{20}$ alkylcarbonyl, benzoyl, aroyl, substituted aroyl, butoxycarbonyl.

$R^2$ is selected from phenyl, mono-, di- or poly- substituted aryl groups, unsubstituted, mono-, di- or poly- substituted naphthyl groups and unsubstituted, mono-, di- or poly- substituted heteroaryl groups (for example but not exclusively thienyl, benzothienyl, furyl, benzofuryl, pyrryl, indolyl, pyridyl, quinolyl, isoquinolyl, pyrimidyl, oxazolyl, isoxazolyl, thiazolyl, isothiazolyl, pyrazolyl, imidazolyl, benzimidazolyl, triazolyl, benzotriazolyl, tetrazolyl). The substituents, of which there may be one or more, for the aryl, naphthyl and heteroaryl groups representing $R^2$ may be hydrogen, linear or branched $C_1$–$C_{20}$ alkyl, $C_3$–$C_{20}$ cycloalkyl, $C_4$–$C_{20}$ bicycloalkyl (for example but not exclusively norbornyl), $C_5$–$C_{20}$ polycycloalkyl (for example but not exclusively adamantyl), linear or branched $C_1$–$C_{20}$ haloalkyl, linear or branched $C_1$–$C_{20}$ perhaloalkyl, linear or branched $C_2$–$C_{20}$ alkenyl (E or Z isomers), linear or branched $C_4$–$C_{20}$ polyalkenyl (any combinations of E or Z isomers), linear or branched $C_2$–$C_{20}$ alkynyl, linear or branched $C_4$–$C_{20}$ polyalkynyl, linear or branched $C_1$–$C_{20}$ hydroxyalkyl, linear or branched $C_1$–$C_{20}$ polyhydroxyalkyl, linear or branched $C_1$–$C_{20}$ alkoxy, linear or branched $C_1$–$C_{20}$ alkylthio, linear or branched $C_1$–$C_{20}$($C_1$–$C_{10}$ alkoxy)alkyl, linear or branched $C_1$–$C_{20}$($C_1$–$C_5$ alkylthio) alkyl, phenyl, aryl, heteroaryl, halogen, hydroxyl, formyl, acetyl, nitrile, carboxyl, $C_1$–$C_{10}$ alkoxycarbonyl, $C_1$–$C_{10}$ N-alkylamido, $C_1$–$C_5$ N,N-dialkylamido, amido, nitro, amino, $C_1$–$C_{20}$ alkylamino, $C_1$–$C_{20}$ dialkylamino, $C_2$–$C_{20}$ dialkenylamino, $C_4$–$C_{20}$ di(polyalkenyl)amino, arylamino, diarylamino, $C_1$–$C_{20}$ alkylarylamino, and cyclic-amino groups (for example but not exclusively aziridino, pyrrolidino, piperidino, linear or branched $C_1$–$C_{20}$ alkylsubstituted piperidino, morpholino, thiomorpholino, indolino, piperazino, linear or branched $C_1$–$C_{20}$ N-alkylpiperazino, linear or branched $C_1$–$C_{20}$ N-hydroxyalkylpiperazino, N-phenylpiperazino, N-arylpiperazino, homopiperidino), arylsulfanyl, aryloxy, arylsulfinyl, arylsulfonyl, linear or branched $C_1$–$C_{20}$ alkylsulfonyl, di-($C_1$–$C_{20}$ alkoxyalkyl) phosphonyl fin addition to those substituents specified for $R^1$. Phenyl, aryl, naphthyl, and heteroaryl ring substituents may be located at the ortho-, meta- or para- positions.

$R^3$ and $R^4$, which may be the same or different, are selected from hydrogen, linear or branched $C_1$–$C_{20}$ alkyl, $C_3$–$C_{20}$ cycloalkyl, $C_4$–$C_{20}$ bicycloalkyl (for example but not exclusively norbornyl), $C_5$–$C_{20}$ polycycloalkyl (for example but not exclusively adamantyl), linear or branched $C_1$–$C_{20}$ haloalkyl, linear or branched $C_1$–$C_{20}$ perhaloalkyl, linear or branched $C_2$–$C_{20}$ alkenyl (E or Z isomers), linear or branched $C_4$–$C_{20}$ polyalkenyl (any combination of E or Z isomers), linear or branched $C_2$–$C_{20}$ alkynyl, linear or branched $C_4$–$C_{20}$ polyalkynyl, linear or branched $C_1$–$C_{20}$ hydroxyalkyl, linear or branched $C_1$–$C_{20}$ polyhydroxyalkyl, linear or branched $C_1$–$C_{20}$ alkoxy, linear or branched $C_1$–$C_{20}$ alkylthio, linear or branched $C_1$–$C_{20}$($C_1$–$C_{10}$ alkoxy)alkyl, linear or branched $C_1$–$C_{20}$($C_1$–$C_5$ alkylthio) alkyl, phenyl, aryl, heteroaryl, halogen, hydroxyl, formyl, acetyl, nitrile, carboxyl, $C_1$–$C_5$ alkoxycarbonyl, $C_1$–$C_5$ N-alkylamido, $C_1$–$C_5$ N,N-dialkylamido, amido, nitro, in addition to those groups specified for $R^1$ and $R^2$ above.

$R^5$ is selected from linear or branched $C_1$–$C_{20}$ alkyl, $C_3$–$C_{20}$ cycloalkyl, $C_4$–$C_{20}$ bicycloalkyl (for example but not exclusively norbornyl), $C_5$–$C_{20}$ polycycloalkyl (for example but not exclusively adamantyl), linear or branched $C_1$–$C_{20}$ haloalkyl, linear or branched $C_1$–$C_{20}$ perhaloalkyl, linear or branched $C_2$–$C_{20}$ alkenyl (E or Z isomers), linear or branched $C_4$–$C_{20}$ polyalkenyl (any combination of E or Z isomers), linear or branched $C_2$–$C_{20}$ alkynyl, linear or branched $C_4$–$C_{20}$ polyalkynyl, linear or branched ($C_{20}$ hydroxyalkyl, linear or branched $C_1$–$C_{20}$ polyhydroxyalkyl, linear or branched $C_1$–$C_{20}$ alkoxy, linear or branched $C_1$–$C_{20}$ alkylthio, linear or branched $C_1$–$C_{20}$($C_1$–$C_{10}$ alkoxy)alkyl, linear or branched $C_1$–$C_{20}$($C_1$–$C_{10}$ alkylthio)alkyl, phenyl, aryl, heteroaryl, halogen, hydroxyl, formyl, acetyl, linear or branched $C_1$–$C_{20}$ alkanoyl, linear or branched $C_3$–$C_{20}$ alkenoyl, linear or branched $C_5$–$C_{20}$ polyalkenoyl, benzoyl, aroyl, heteroaroyl, nitrile, formyl, carboxyl, linear or branched $C_1$–$C_{20}$ alkoxycarbonyl, $C_1$–$C_{20}$ N-alkylamido, $C_1$–$C_{20}$ N,N-dialkylamido, amido, nitro, amino, $C_1$–$C_{20}$ alkylamino, $C_1$–$C_{20}$ dialkylamino, $C_2$–$C_{20}$ dialkenylamino, $C_4$–$C_{20}$ di(polyalkenyl)amino, arylamino, diarylamino, $C_1$–$C_{20}$ alkylarylamino, and cyclic-amino groups (for example but not exclusively aziridino, pyrrolidino, piperidino, morpholino, thiomorpholino, indolino, piperazino, linear or branched $C_1$–$C_{20}$ N-alkylpiperazino, linear or branched $C_1$–$C_{20}$ N-hydroxyalkylpiperazino, N-phenylpiperazino, N-arylpiperazino, homopiperidino, N-indolinyl), arylsulfanyl, aryloxy, arylsulfinyl, arylsulfonyl, linear or branched $C_1$–$C_{20}$ alkylsulfonyl, di-($C_1$–$C_{20}$ alkoxyalkyl) phosphonyl in addition to those substituents specified for $R^1$ and $R^2$.

One or both of $R^7$ and $R^9$, which may be the same or different is selected from $C_1$–$C_{20}$ N,N-alkylamido, $C_1$–$C_{20}$ N,N-dialkylamido, amido, nitro, amino, $C_1$–$C_{20}$ alkylamino, $C_1$–$C_{20}$ dialkylamino, $C_2$–$C_{20}$ dialkenylamino, $C_4$–$C_{20}$ di(polyalkenyl)amino, arylamino, diarylamino, $C_1$–$C_{20}$ alkylarylamino, and cyclic-amino groups (for example but not exclusively aziridino, pyrrolidino, piperidino, morpholino, thiomorpholino, indolino, piperazino, linear or branched $C_1$–$C_{20}$ N-alkylpiperazino, linear or branched $C_1$–$C_{20}$ N-hydroxyalkylpiperazino, N-phenylpiperazino, N-arylpiperazino, homopiperidino, N-indolinyl, N- 1,2,3,4-tetrahydrocarbazolyl, N-1,2,3,4,4a,9a-hexahydrocarbazolyl, N-1,2,3,4-tetrahydroquinolyl). Where only one of $R^7$ or $R^9$ is selected from the above nitrogen containing substituents, the other group $R^7$ or $R^9$ is selected from those substituents specified for $R^1$, $R^2$, $R^5$, $R^6$, $R^8$ and $R^{10}$.

$R^6$, $R^8$, $R^{10}$, $R^{11}$, $R^{12}$, $R^{14}$, $R^{15}$, $R^{17}$ and $R^{18}$ which may be the same or different, are selected from hydrogen, linear or branched $C_1$–$C_{20}$ alkyl, $C_3$–$C_{20}$ cycloalkyl, $C_4$–$C_{20}$ bicycloalkyl (for example but not exclusively norbornyl), $C_5$–$C_{20}$ polycycloalkyl (for example but not exclusively adamantyl), linear or branched $C_1$–$C_{20}$ haloalkyl, linear or branched $C_1$–$C_{20}$ perhaloalkyl, linear or branched $C_2$–$C_{20}$ alkenyl (E or Z isomers), linear or branched $C_4$–$C_{20}$ polyalkenyl (any combination of E or Z isomers), linear or branched $C_2$–$C_{20}$ alkynyl, linear or branched $C_4$–$C_{20}$ polyalkynyl, linear or branched $C_1$–$C_{20}$ hydroxyalkyl, linear or branched $C_1$–$C_{20}$ polyhydroxyalkyl, linear or branched $C_1$–$C_{20}$ alkoxy, linear or branched $C_1$–$C_{20}$ alkylthio, linear or branched $C_1$–$C_{20}$($C_1$–$C_{10}$ alkoxy)alkyl, linear or branched $C_1$–$C_{20}$($C_1$–$C_{10}$ alkylthio)alkyl, phenyl, aryl, heteroaryl, halogen, hydroxyl, formyl, acetyl, linear or branched $C_1$–$C_{20}$ alkanoyl, linear or branched $C_3$–$C_{20}$ alkenoyl, linear or branched $C_5$–$C_{20}$ polyalkenoyl, benzoyl, aroyl, heteroaroyl, nitrile, carboxyl, formyl, $C_1$–$C_{20}$ alkoxycarbonyl, $C_1$–$C_{20}$ N-alkylamido, $C_1$–$C_{20}$ N,N-dialkylamido, amido, nitro, amino, $C_1$–$C_{20}$ alkylamino, $C_1$–$C_{20}$ dialkylamino, $C_2$–$C_{20}$ dialkenylamino, $C_4$–$C_{20}$ di(polyalkenyl)amino, arylamino, diarylamino, $C_1$–$C_{20}$ alkylarylamino, and cyclic-amino groups (for example but not exclusively aziridino, pyrrolidino, piperidino, morpholino, thiomorpholino, indolino, piperazino, linear or branched $C_1$–$C_{20}$ N-alkylpiperazino, linear or branched $C_1$–$C_{20}$ N-hydroxyalkylpiperazino, N-phenylpiperazino, N-arylpiperazino, homopiperidino, N-indolinyl), arylsulfanyl, aryloxy, arylsulfinyl, arylsulfonyl, linear or branched $C_1$–$C_{20}$ alkylsulfonyl, di-($C_1$–$C_{10}$ alkoxyalkyl) phosphonyl in addition to those substituents specified for $R^1$ and $R^2$ and $R^5$ $R^{16}$ of which there may be one or more, the same or different, are selected from hydrogen, linear or branched $C_1$–$C_{20}$ alkyl, $C_3$–$C_{20}$ cycloalkyl, $C_4$–$C_{20}$ bicycloalkyl (for example but not exclusively norbornyl), $C_5$–$C_{20}$ polycycloalkyl (for example but not exclusively adamantyl), linear or branched $C_1$–$C_{20}$ haloalkyl, linear or branched $C_2$–$C_{20}$ perhaloalkyl, linear or branched $C_2$–$C_{20}$ alkenyl (E or Z isomers), linear or branched $C_4$–$C_{20}$ polyalkenyl (any combination of E or Z isomers), linear or branched $C_2$–$C_{20}$ alkynyl, linear or branched $C_4$–$C_{20}$ polyalkynyl, linear or branched $C_1$–$C_{20}$ hydroxyalkyl, linear or branched $C_1$–$C_{20}$ polyhydroxyalkyl, linear or branched $C_1$–$C_{20}$ alkoxy, linear or branched $C_1$–$C_{20}$ alkylthio, linear or branched $C_1$–$C_{20}$ ($C_1$–$C_{10}$ alkoxy)alkyl, linear or branched $C_1$–$C_{20}$($C_1$–$C_5$ alkylthio)alkyl, phenyl, aryl, heteroaryl, halogen, hydroxyl, formyl, acetyl, linear or branched $C_1$–$C_{20}$ alkanoyl, linear or branched $C_3$–$C_{20}$ alkenoyl, linear or branched $C_5$–$C_{20}$ polyalkenoyl, benzoyl, aroyl, heteroaroyl, nitrile, carboxyl, formyl, $C_1$–$C_{20}$ alkoxycarbonyl, $C_1$–$C_{20}$ N-alkylamido, $C_1$–$C_{20}$ N,N-dialkylamido, amido, nitro, amino, $C_1$–$C_{20}$ alkylamino, $C_1$–$C_{20}$ dialkylamino, $C_2$–$C_{20}$ dialkenylamino, $C_4$–$C_{20}$ di(polyalkenyl)amino, arylamino, diarylamino, $C_1$–$C_{20}$ alkylarylamino, and cyclic-amino groups (for example but not exclusively aziridino, pyrrolidino, piperidino, morpholino, thiomorpholino, indolino, piperazino, linear or branched $C_1$–$C_{20}$ N-alkylpiperazino, linear or branched $C_1$–$C_{20}$ N-hydroxyalkylpiperazino, N-phenylpiperazino, N-arylpiperazino, homopiperidino, N-indolinyl), arylsulfonyl, aryloxy, arylsulfinyl, arylsulfonyl, linear or branched $C_1$–$C_{20}$ alkylsulfonyl, di-($C_1$–$C_{10}$ alkoxyalkyl)phosphonyl in addition to those substituents specified for $R^1$ through to and including $R^{18}$.

In addition to the 2H-naphtho[1,2-b]pyran compounds of formula I, the present invention includes the pyrans of the general formula V, VI, VII and VIII.

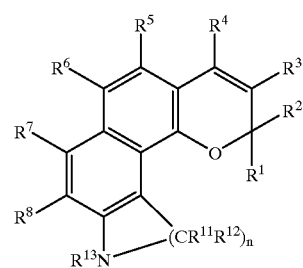

V

VI

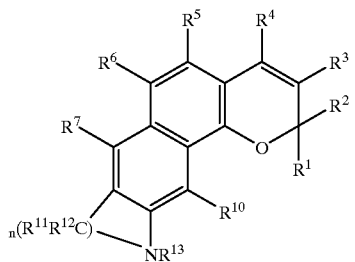

VII

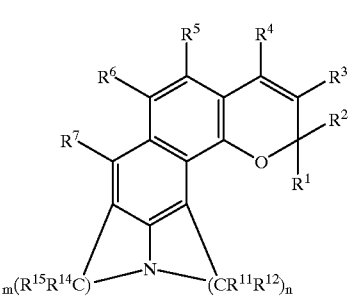

VIII

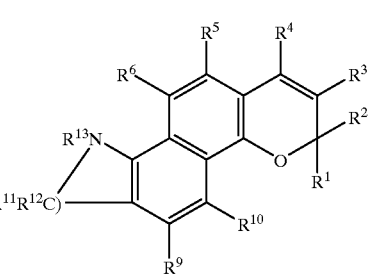

In addition to the 2H-naphtho[1,2-b]pyran compounds of formula I, the substituents $R^5$ and $R^6$ or $R^7$ and $R^8$ or $R^8$ and $R^9$ or $R^9$ and $R^{10}$ may each be conjoined by a four carbon unit containing one or more substituents represented by $R^{16}$ to provide benzo fused naphthopyrans of the general formula IX and X and XI and XII

IX

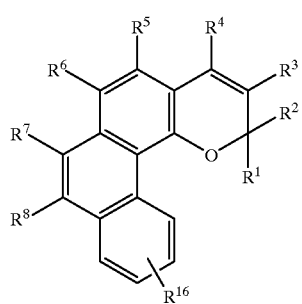

X

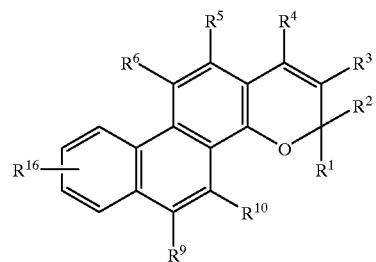

XI

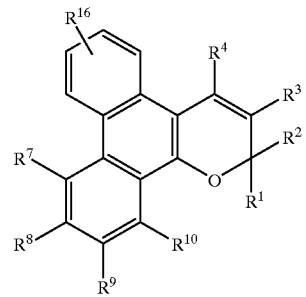

XII

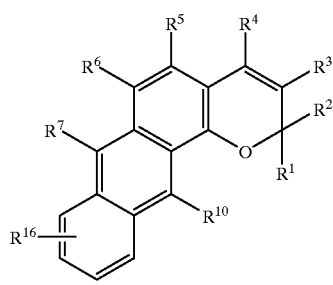

In addition to the 21H-naphtho[1,2b]pyran compounds of formula I, the present invention includes the heterocyclic fused pyrans of the general formula XIII and XIV and XV and XVI and XVII and XVIII and XIX.

XIII

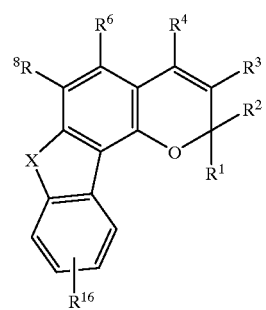

XIV

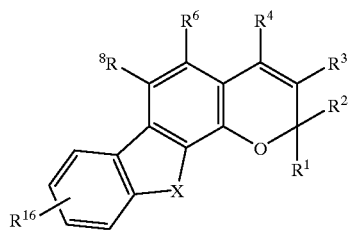

-continued

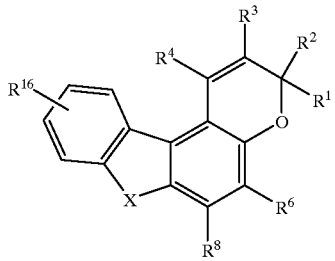

XV

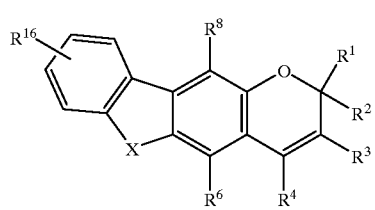

XVI

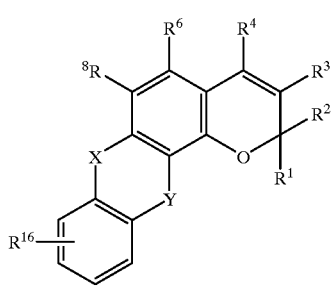

XVII

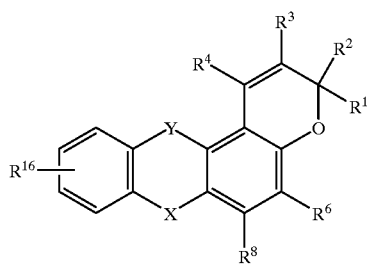

XVIII

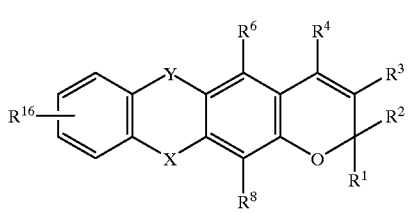

XIX

The function (X) in the structures XIII–XIX is selected from a single bond, O, S, SO, $SO_2$, Se, NH, N—O, N-linear or branched $C_1$–$C_{20}$ alkyl, N-$C_3$–$C_{20}$ cycloalkyl, N-$C_4$–$C_{20}$ bicycloalkyl, N-$C_5$–$C_{20}$ polycycloalkyl, N-linear or branched $C_1$–$C_{10}$ hydroxyalkyl, N-linear or branched $C_1$–$C_{10}$ haloalkyl, N-linear or branched $C_1$–$C_{10}$ perhaloalkyl, N-phenyl, N-$C_1$–$C_{10}$ linear or branched alkylsulfonyl, N-aryl, N-tosyl, N-acyl, N-benzoyl, N-aroyl, N-butoxycarbonyl, P-linear or branched $C_1$–$C_{10}$ alkyl, P-phenyl, P-aryl, P- substituted aryl, P(O)-linear or branched $C_1$–$C_{10}$ alkyl, P(O)O-linear or branched $C_1$–$C_{10}$ alkyl, P(O)O-phenyl, P(O)O-aryl, C=S, C=O, C=$NR^{16}$, $CH_2$, $CHR^{16}$, $C(OH)R^{16}$, $CR^{17}R^{18}$.

The function (Y) in the structures XVII-XIX is selected from a single bond, O, S, SO, $SO_2$, Se, NH, N—O, N-linear or branched $C_1$–$C_{20}$ alkyl, N-$C_3$—$C_{20}$ cycloalkyl, N-$C_4$–$C_{20}$ bicycloalkyl, N-$C_5$–$C_{20}$ polycycloalkyl, N-linear or branched $C_1$–$C_{10}$ hydroxyalkyl, N-linear or branched $C_1$–$C_{10}$ haloalkyl, N-linear or branched $C_1$–$C_{10}$ perhaloalkyl, N-phenyl, N-$C_1$–$C_{10}$ linear or branched alkylsulfonyl, N-aryl, N-tosyl, N-acyl, N-benzoyl, N-aroyl, N-butoxycarbonyl, P-linear or branched $C_1$–$C_{10}$ alkyl, P-phenyl, P-aryl, P- substituted aryl, P(O)-linear or branched $C_1$–$C_{10}$ alkyl, P(O)O-linear or branched $C_1$–$C_{10}$ alyl, P(O)O-phenyl, P(O)O-aryl, C=S, C=O, C=$NR^{16}$, $CH_2$, $CHR^{16}$, $C(OH)R^{16}$, $CR^{17}R^{18}$ The 1-naphthols and related hydroxy compounds are either commercially available or obtained by known synthetic methods, or derived by such methods by persons skilled in the art of organic synthesis. In particular, the application of the Stobbe condensation to prepare numerous substituted 1-naphthols has been discussed (see Organic Reactions, Wiley, New York, 1951, volume 6, p. 1). Other routes to useful hydroxy compounds include the application of Bradsher cycloaddition methodology e.g. R F. Frank et al., *J Chem. Soc., Chem. Commun.,* 1984, 761.

The synthesis of the propargyl alcohols has been described in the scientific literature, see for example T. F. Rutledge in 'Acetylenic Compounds,' Reinhold, New York, 1968.

The combination of the substituted 1-naphthols and the propargyl alcohols to afford the naphthopyran is well established (Scheme), see for example L. Merlini in 'Advances in Heterocyclic Chemistry,' Academic Press, 1975, vol. 18, p. 159; R Guglielmetti in 'Photochromism: Molecules and Systems,' Studies in Organic Chemistry 40, eds. H. Durr and H. Bouas-Laurent, Elsevier, 1990. chp. 8; J. D. Hepworth, C. D. Gabbutt, B. M. Heron in 'Comprehensive Heterocyclic Chemistry A,' eds. A P Katritzky, C. W. Rees, E. E. V. Scriven, Pergamon, 1996, vol. 5, p. 351.

Scheme

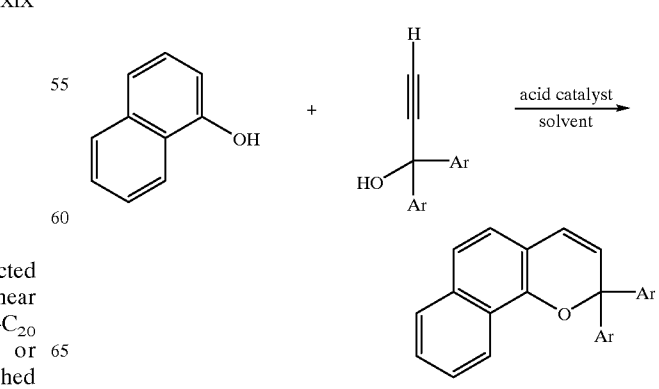

The acid catalyst may be selected from alumina (e.g. Brockmann 1), acetic acid, trifluoroacetic acid, silica, clays (e.g. montmorillonite, tonsil), acidic exchange resins, alkylbenzene sulfonic acids (e.g. toluenesulfonic acid).

Organic solvents frequently employed for the reaction include benzene, toluene, xylene, and relatively high boiling alkanes and ethers.

In order that the invention may be more fully understood, reference will now be made to the following Examples, by way of illustration only.

EXAMPLES

The following examples have been selected to illustrate the claimed effect, but in no way limit the claim.

1. Methyl 9-dimethylamino-2-phenyl-2-(4-piperidinophenyl)-2H-naphtho[1,2-b]pyran-5-carboxylate A solution of methyl 6-dimethylamino-4-hydroxy-2-naphthoate (5 mmol) and 1-phenyl-1-(4-piperidinophenyl) prop-2-yn-1-ol (5 mmol) in toluene (60 cm$^3$) containing acidic alumina (Brockrmann 1) (5 g) was refluxed for 90 minutes. The cooled solution was filtered and the alumina residue washed well with ethyl acetate (5×40 cm$^3$). Removal of the dried solvent gave a brown gum which was flash chromatographed using 30% ethyl acetate in hexane as the eluent to give an off-white solid. Recrystallisation from ethyl acetate and hexane gave the title compound (m.p. =155–156.5° C.).

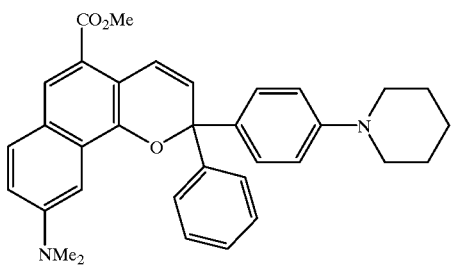

The following compounds were obtained in a similar fashion from the requisite starting materials:

2. Methyl 9-dimethylamino-2,2-di(4-piperidinophenyl)-2S-naphtho[1,2-b]pyran-5-carboxylate (m.p. =187–189° C.) from methyl 6-dimethylamino4-hydroxy-2-naphthoate and 1,1-di(4-piperidinophenyl)prop-2-yn-1-ol.

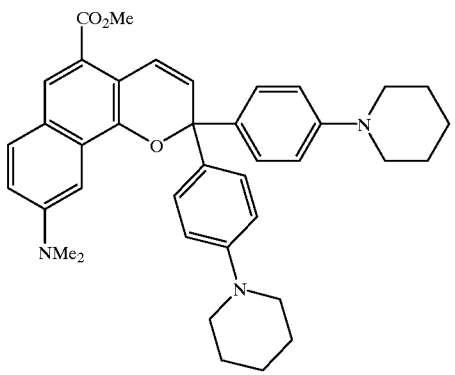

3. Methyl 9-morpholino-2-(4-dimethylaminophenyl)-2-(4-methoxyphenyl)-2H-naphtho[1,2-b]pyran-5-carboxylate (m.p. =208.5–211° C.) from methyl 6-morpholino-4-hydroxy-2-naphthoate and ]-(4-dimethylaminophenyl)-1-(4-methoxyphenyl)-prop-2-yn-1-ol.

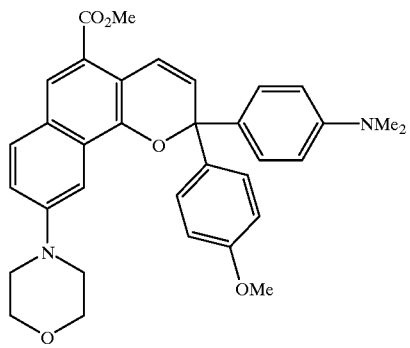

4. Methyl 9-dimethylamino-2,2-di(4-dimethylaminophenyl)-2H-naphtho[1,2-b]pyran-5-carboxylate (m.p. =224.5–226° C.) from methyl 6-dimethylamino-4-hydroxy-2-naphthoate and 1,1 -di(4-dimethylaminophenyl)prop-2-yn-1-ol.

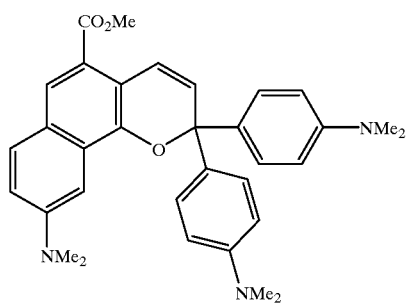

5. 2-Phenyl-2-(4-piperidinophenyl)-2H-pyrano[2,3a]xanthen-12-one (m.p. =153–155° C.) from 1-hydroxyxanthone and 1-phenyl-1-(4-piperidinophenyl)-prop2-yn-1-ol.

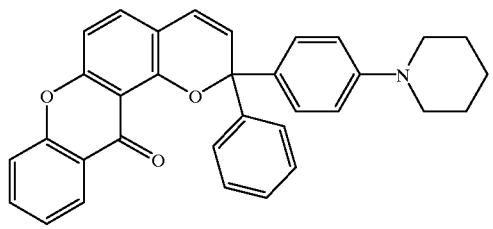

6. 2-Phenyl-2-(4-piperidinophenyl)-2H-1-benzothieno[2,3-h]-1-benzopyran (m.p. =144–146° C.) from 4-hydroxydibenzothiophene and 1-(4-piperidinophenyl)-1-phenylprop-2-yn-1-ol.

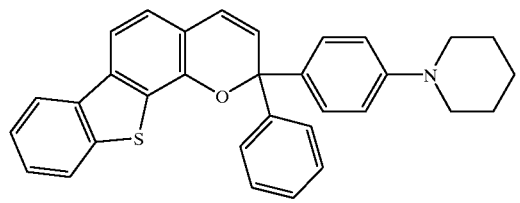

7. Methyl 9-dimethylamino-2-phenyl-2-(4-pyrrolidinophenyl)-2H-naphtho[1,2-b]pyran-5-carboxylate (.p. =176–178° C.) from methyl 6-dimethylamino-4-hydroxy-2-naphthoate and 1-phenyl-1-(4-pyrrolidinophenyl)prop-2-yn-1-ol.

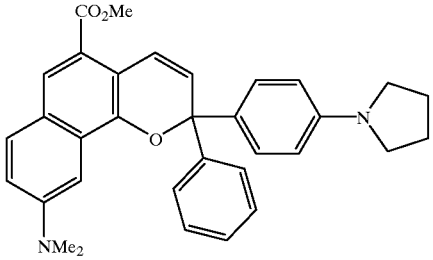

What is claimed is:

1. A photochromic, grey colouring 2H-naphtho[1,2-b]pyran of the formula I

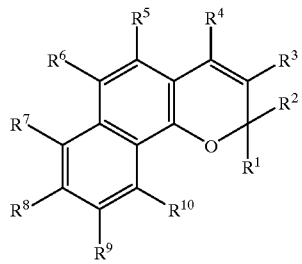

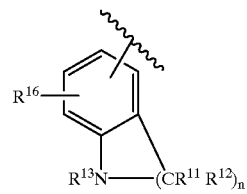

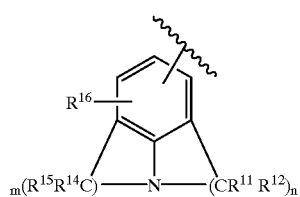

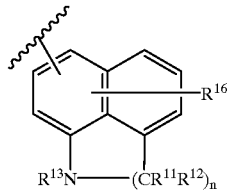

wherein $R^1$ is selected from mono-, di- or poly-substituted aryl groups, mono-, di- or poly-substituted naphthyl groups and mono-, di- or poly-substituted heteroaryl groups, wherein at least on substitutent is selected from amino, $C_1$–$C_{20}$ and $C_6$–$C_{20}$ alkylamino, $C_1$–$C_{20}$ and $C_6$–$C_{20}$ dialkylamino, $C_2$–$C_{20}$ dialkenylamino, $C_2$–$C_{20}$ or $C_4$–$C_{20}$ di(polyalkenyl)amino, arylamino, diarylamino, $C_1$–$C_{20}$ alkylarylamino, tetra($C_1$–$C_{10}$ liner or branched alkyl) guanidino and cyclic-amino groups; $R^2$ is selected from phenyl, mono-, di- or poly-substituted aryl groups, unsubstituted, mono-, di- or poly-substituted naphthyl groups, and unsubstituted, mono-, di- or poly-substituted heteroaryl groups, wherein, if substituted, the substituents are selected from those substituents for $R^1$ or are linear or branched $C_1$–$C_{10}$ or $C_6$–$C_{20}$ alkyl, $C_3$–$C_{20}$ cycloalkyl, $C_2$–$C_{20}$ bicycloalkyl, $C_5$–$C_{10}$ polycycloalkyl, linear or branched $C_1$–$C_{20}$ or $C_6$–$C_{20}$ haloalkyl, linear or branched $C_1$–$C_{20}$ perhaloalkyl, linear or branched $C_2$–$C_{20}$ alkenyl, linear or branched $C_1$–$C_{20}$ polyalkenyl, linear or branched $C_2$–$C_{20}$ alkynyl, linear or branched $C_4$–$C_{20}$ polyalkynyl, linear or branched $C_1$–$C_{20}$ or $C_6$–$C_{20}$ hydroxyalkyl, $C_1$–$C_{20}$ polyhydroxyalkyl, linear or branched $C_1$–$C_{20}$ or $C_6$–$C_{20}$ alkoxy, linear or branched $C_1$–$C_{20}$ alkylthio, linear or branched $C_1$–$C_{20}$ or $C_6$–$C_{20}$($C_1$–$C_{10}$ or $C_6$–$C_{10}$ alkoxy) alkyl, linear or branched $C_1$–$C_{20}$($C_1$–$C_5$ alkylthio)alkyl, phenyl, aryl, heteroaryl, halogen, hydroxyl, formyl, acetyl, nitrile, carboxyl, $C_1$–$C_{10}$ alkoxycarbonyl, $C_1$–$C_{10}$ N-alkylamido, $C_1$–$C_5$ N,N-dialkylamido, amido, nitro, arylsulfanyl, aryloxy, arylsulfinyl, arylsulfonyl, linear or branched $C_1$–$C_{20}$ alkylsulfonyl and di-($C_1$–$C_{20}$ alkoxyalkyl) phosphonyl or $R^1$ and/or $R^2$ may also be selected from the fused saturated heterocycles II, III and IV in which n and m are integers between 2 and 5 and are the same or different;

wherein $R^{13}$ is selected from linear or branched $C_1$–$C_{20}$ alkyl, $C_3$–$C_{20}$ cycloalkyl, $C_4$–$C_{20}$ bicycloalkyl, $C_5$–$C_{20}$ polycycloalkyl, linear or branched $C_1$–$C_{20}$ hydroxyalkyl, linear or branched $C_1$–$C_{20}$ haloalkyl, linear or branched $C_1$–$C_{20}$ perhaloalkyl, phenyl, $C_1$–$C_{20}$ linear or branched alkylsulfonyl, aryl, tosyl, arylsulfonyl, acyl, linear or branched $C_1$–$C_{20}$ alkylcarbonyl, benzoyl, aroyl, substituted aroyl and butoxycarbonyl.

$R^3$ is $R^1$ or $R^2$ or is selected from hydrogen, linear or branched $C_1$–$C_{20}$ alkyl, $C_3$–$C_{20}$ cycloalkyl, $C_2$–$C_{20}$ bicycloalkyl, $C_5$–$C_{20}$ polycycloalkyl linear or branched $C_1$–$C_{20}$ haloalkyl, linear or branched $C_1$–$C_{20}$ perhaloalkyl, linear or branched $C_2$–$C_{20}$ alkenyl, linear or branched or $C_1$–$C_{20}$ polyalkenyl, linear or branched $C_2$–$C_{20}$ alkynyl, linear or branched $C_4$–$C_{20}$ polyalkynyl, linear or branched $C_1$–$C_{20}$ hydroxyalkyl, linear or branched $C_1$–$C_{20}$ polyhydroxyalkyl, linear or branched $C_1$–$C_{20}$ alkoxy, linear or branched $C_1$–$C_{20}$ alkylthio, linear or branched $C_1$–$C_{20}$ ($C_1$–$C_{10}$ alkoxy)alkyl, linear or branched $C_1$–$C_{20}$($C_1$–$C_5$ alkylthio)alkyl, phenyl, aryl, heteroaryl, halogen, hydroxyl, formyl, acetyl, nitrile, carboxyl, $C_1$–$C_5$ alkoxycarbonyl, $C_1$–$C_5$ N-alkylamido, $C_1$–$C_5$ N,N-dialkylamido, amido and nitro; $R^4$ is hydrogen; $R^5$ is selected from $R^2$ or from the substituents to the substituted aryl groups, substituted naphthyl groups and substituted heteroaryl groups of $R^1$ and $R^2$, or from linear or branched $C_1$–$C_{20}$($C_1$–$C_{10}$ alkylthio)alkyl, linear or branched $C_1$–$C_{20}$ alkenoyl, linear or branched $C_3$–$C_{20}$ alkanoyl, linear or branched $C_5$–$C_{20}$ polyalkenoyl, benzoyl, aroyl, heteroaroyl, linear or branched $C_1$–$C_{20}$ alkoxycarbonyl, $C_1$–$C_{20}$ N-alkylamido and $C_1$–$C_{20}$ N,N-dialkylamido; at least one of $R^7$ and $R^9$, which may be the same or different, is selected from $C_1$–$C_{20}$ N-alkylamido, $C_1$–$C_{20}$ N,N-dialkylamido, amido, nitro, amino, $C_1$–$C_{20}$ alkylamino, $C_1$–$C_{20}$ dialkylamino, $C_2$–$C_{20}$ dialkenylamino, $C_4$–$C_{20}$ di(polyalkenyl)amino, arylamino, diarylamino, $C_1$–$C_{20}$ alkylarylamino, and cyclicamino groups, wherein where only one of $R^7$ or $R^9$ is as defined above, the other group $R^7$ or $R^9$ is selected from those substituents specified for $R^1$, $R^2$, $R^5$, $R^6$, $R^8$ and $R^{10}$, $R^6$, $R^8$, $R^{10}$, $R^{11}$, $R^{12}$, $R^{14}$, $R^{15}$, which may be the same or different, are selected from those substituents of $R^1$, $R^2$, $R^5$ and hydrogen;

$R^{16}$ of which there may be one or more, the same or different are each as defined in any of $R^1$ to $R^{15}$ inclusive or wherein the substituents $R^5$ and $R^6$ or $R^7$ and $R^8$ or $R^8$ and $R^9$ or $R^9$ and $R^{10}$ are each conjoined by a four carbon unit containing one or more substituents according to $R^{16}$ to provide benzo fused naphtopyrans;

wherein said 2H-naptho[1,2-b]pyran exhibits a grey color.

2. A 2H-naphtho[1,2-b]pyran according to claim 1, wherein the nitrogen containing substituent of $R^1$ is at the position para to the point of attachment to the pyran ring.

3. A 2H-naphtho[1,2-b]pyran according to claim 1, wherein the aryl groups, the naphthyl groups or the heteroaryl groups of $R^1$ are further substituted by at least one substituent selected from linear or branched or $C_1$–$C_{20}$ or $C_6$–$C_{20}$ alkyl, $C_3$–$C_{20}$ cycloalkyl, $C_4$–$C_{20}$ bicycloalkyl, $C_5$–$C_{20}$ polycycloalkyl, linear or branched $C_1$–$C_{20}$ or $C_6$–$C_{20}$ haloalkyl, linear or branched $C_1$–$C_{20}$ perhaloalkyl, linear or branched $C_2$–$C_{20}$ alkenyl, linear or branched $C_2$–$C_{20}$ or $C_4$–$C_{20}$ polyalkenyl, linear or branched $C_2$–$C_{20}$ alkenyl, linear or branched $C_4$–$C_{20}$ polyalkenyl, linear or branched $C_1$–$C_{20}$ or $C_6$–$C_{20}$ hydroxyalkyl, linear or branched $C_1$–$C_{20}$ polyhydroxyalkyl, linear or branched $C_1$–$C_{20}$ or $C_6$–$C_{20}$ alkoxy, linear or branched $C_1$–$C_{20}$ alkylthio, linear or branched $C_1$–$C_{20}$ or $C_6$–$C_{20}$($C_1$–$C_5$ alkoxy)alkyl, linear or branched $C_1$–$C_{20}$($C_1$–$C_5$ alkylthio)alkyl, phenyl, aryl, heteroaryl, halogen, hydroxyl, formyl, acetyl, nitrile, carboxyl, $C_1$–$C_5$ alkoxycarbonyl, $C_1$–$C_5$ alkoxycarbonyl, $C_1$–$C_5$ N-alkylamido, $C_1$–$C_5$ N,N-dialkylamido, amido, nitro, arylsulfanyl, aryloxy, arylsulfinyl, arylsulfonyl, linear or branched $C_1$–$C_{20}$ alkylsulfonyl and di-($C_1$–$C_{20}$ alkoxyalkyl)phosphonyl, each being the same or different.

4. A 2H-naphtho[1,2-b]pyran according to claim 1, wherein the substituted heteroaryl groups are selected from thienyl, benzothienyl, furyl, benzofuryl, pyrryl, indolyl, pyridyl, quinolyl, isoquinolyl, pyrimidyl, oxazolyl, isoxazolyl, thiazolyl, isothiazolyl, pyrazolyl, imidazolyl, benzimidazolyl, triazolyl, benzotriazolyl and tetrazolyl.

5. A 2H-naphtho[1,2-b]pyran according to claim 1, wherein the cyclic-amino group of $R^1$ to $R^6$ inclusive, $R^8$ and $R^{10}$ to $R^{18}$ inclusive is selected from aziridino, pyrrolidino, piperidino, linear or branched $C_1$–$C_{20}$ alkylsubstituted piperidino, morpholino, thiomorpholino, indolino, piperazino, linear or branched $C_1$–$C_{20}$ N-alkylpiperazino, linear or branched $C_1$–$C_{20}$ N-hydroxyalkylpiperazino, N-phenylpiperazino, N-arylpiperazino and homopiperidino.

6. A 2H-naphtho[1,2-b]pyran according to claim 1, wherein the cyclic-amino group of $R^7$ and/or $R^9$ is selected from aziridino, pyrrolidino, pipeeridino, morpholino, thiomorpholino, indolino, piperazino, linear or branched $C_1$–$C_{20}$ N-alkylpiperazino, linear or branched $C_1$–$C_{20}$ N-hydroxyalkylpiperazino, N-phenylpiperazino, N-arylpiperazino, homopiperidino, N-indolinyl, N-1,2,3,4-tetrahydrocarbazolyl, N-1,2,3,4,4a,9a-hexahydrocarbazolyl, N-1,2,3,4-tetrahydroquinolyl.

7. A 2H-naphtho[1,2-b]pyran according to claim 1, wherein the $C_4$–$C_{20}$ bicycloalkyl group is norbornyl and the $C_5$–$C_{20}$ polycycloalkyl group is adamantyl.

8. A photochromic grey colouring pyran of the general formula V, VI, VII or VIII

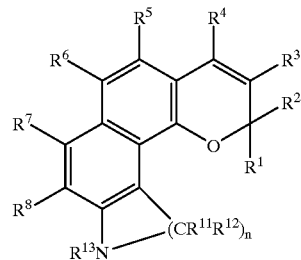

V

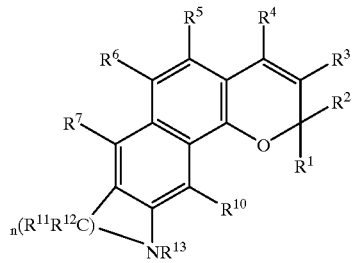

VI

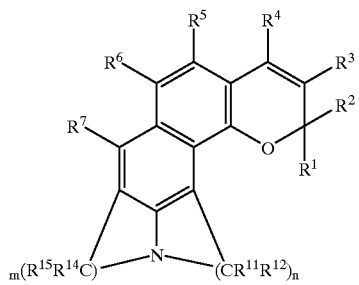

VII

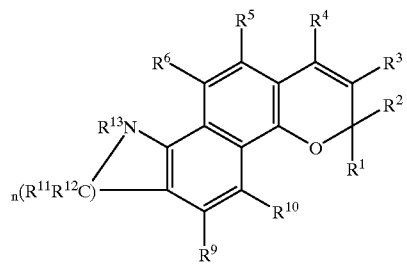

VIII wherein $R^1$ to $R^{15}$ inclusive are as defined according to claim 1.

9. A photochromic grey colouring benzo fused naphthopyran of the general formula XI or XII,

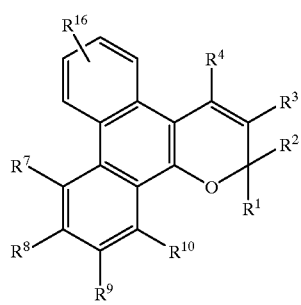

XI

-continued

XII
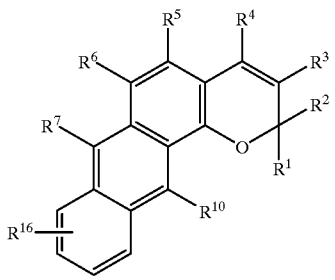

wherein, R¹ to R¹⁰ inclusive and R¹⁶ are as defined in claim 1.

10. A photochromic grey colouring heterocyclic fused pyran of the general formula XIII, XIV, XV, XVI, XVII, XVIII or XIII
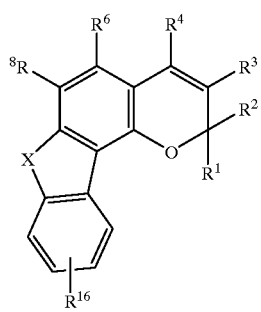

XIV

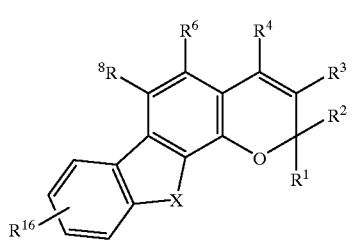

XV

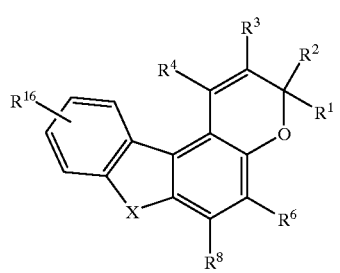

XVI

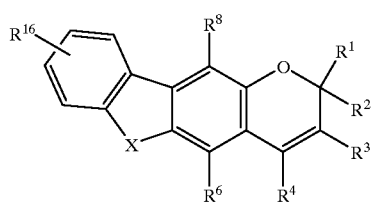

-continued

XVII
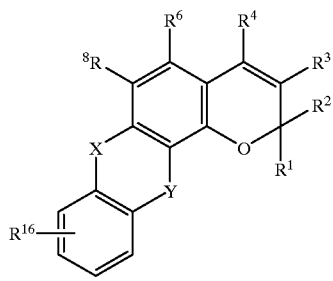

XVIII

XIX

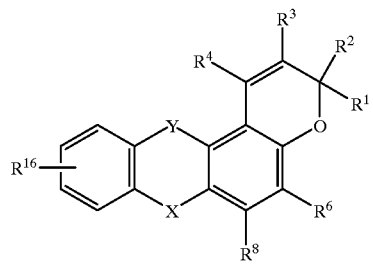

wherein the function (X) is selected from a single bond. O, S, SO, SO₂, Se, NH, N—O, N-linear or branched $C_1$–$C_{20}$ alkyl, N-$C_3$–$C_{20}$ cycloalkyl, N-$C_4$–$C_{20}$ bicycloalkyl, N-$C_3$–$C_{20}$ polycycloalkyl, N-linear or branched $C_1$–$C_{10}$ hydroxyalkyl N-linear or branched $C_1$–$C_{10}$ haloalkyl, N-linear or branched $C_1$–$C_{10}$ perhaloalkyl, N-phenyl, N-$C_1$–$C_{10}$ linear or branched alkysulfonyl, N-aryl, N-tosyl, N-acyl, N-benzoyl, N-aroyl, N-butoxycarbonyl, P-linear or branched $C_1$–$C_{10}$ alkyl, P- phenyl, P-aryl, P-substituted aryl, P(O)-linear or branched $C_1$–$C_{10}$ alkyl, P(O)O-linear or branched $C_1$–$C_{10}$ alkyl, P(O)O-phenyl, P(O)O-aryl, C=S, C=O, C=NR¹⁶, CH₂, CHR¹⁶, C(OH)R¹⁶ and CR¹⁷R¹⁸; the function (Y) is selected from X and may be the same or different, and wherein R¹ to R⁶ inclusive, R⁸, and R¹⁶ are as defined in any of claims 1 to 7, and wherein R¹⁷ and R¹⁸, which may be the same or different are selected from hydrogen or from those substituents of R¹, R² or R⁵ as defined in claim 1.

11. An ink including a pyran according to claim 1.

12. A fuel including a pyran according to claim 1.

13. A polymeric host material including a pyran according to claim 1.

14. A polymeric host material according to claim 13, wherein the material is a plastic or glass.

15. A window, an ophthalmic lens, a sunglass lens, a protective visor, a screen, a film, a container, a mirror or a vehicle body panel including a polymeric host material according to claim 13.

* * * * *